United States Patent [19]
Curtis

[11] Patent Number: 5,224,386
[45] Date of Patent: Jul. 6, 1993

[54] TENSILE TESTING GRIP APPARATUS

[76] Inventor: John M. Curtis, R.D. 5, Box 35, Kittanning, Pa. 16201

[21] Appl. No.: 749,707

[22] Filed: Aug. 26, 1991

[51] Int. Cl.$^5$ ............................................. G01N 3/08
[52] U.S. Cl. ........................................ 73/833; 73/860
[58] Field of Search ............... 73/857, 856, 860, 859, 73/831, 833, 826; 279/8, 34

[56] References Cited

U.S. PATENT DOCUMENTS

| | | | |
|---|---|---|---|
| 3,559,469 | 2/1971 | Stonebridge et al. | 73/831 |
| 4,452,088 | 6/1984 | Whittenberger et al. | 73/833 X |

Primary Examiner—Jerry W. Myracle
Attorney, Agent, or Firm—Lawrence G. Zurawsky; Thomas F. Shanahan

[57] ABSTRACT

Grip apparatus for tensile strength testing of geosynthetic materials includes a pair of opposing first and second grip bars slidably mounted in a frame. Selectively operable locking elements carried on the frame and the first grip bar enable selective fixation of the first grip bar at a desired position with respect to the second grip bar when inserting or removing or loading test specimens. Various constructions of grip bars, and grip jaws mounted on the bars, are provided, including replaceable high friction surface rods, grip surfaces with alternating grooves and shoulder surfaces, and easily replaceable L-shaped grip jaws that do not require disassembly of the apparatus. A plurality of actuating shafts impart movement and grip forces to each grip bar, with the actuating pumps for the shafts being operable simultaneously, separately, synchronously or asynchronously. Preferred actuating pumps for the shafts include fluid driven pumps and, in particular, air actuated pumps providing internal transduction of the air pressure to hydraulic pressure and providing substantial amplification of actuating pressure delivered to the actuator shafts, with improved control in the incremental and decremental pressures applied.

29 Claims, 5 Drawing Sheets

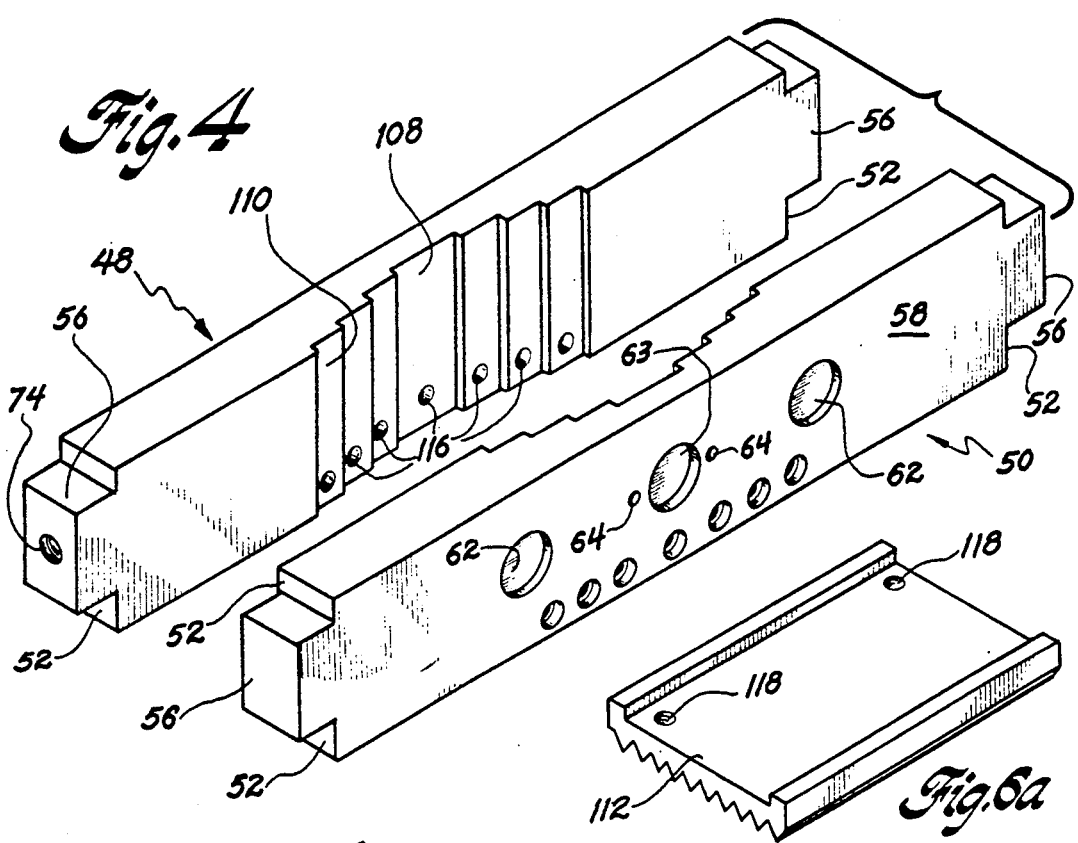
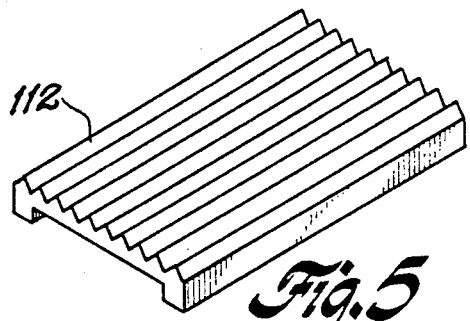
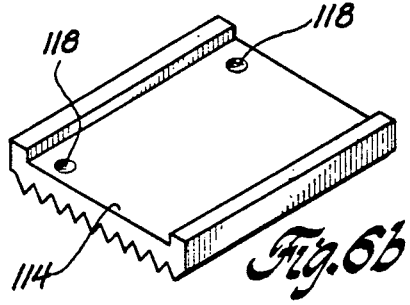
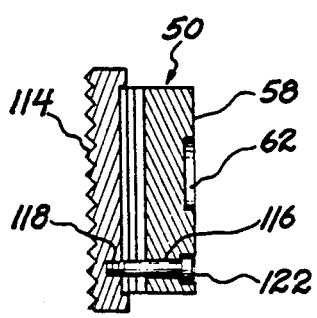
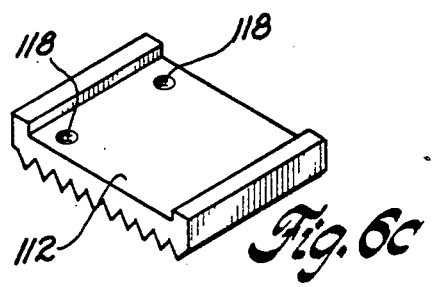
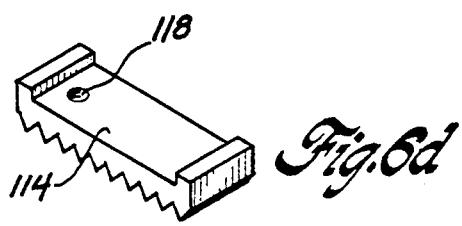

TENSILE TESTING GRIP APPARATUS

FIELD OF THE INVENTION

This invention relates to apparatus for gripping and applying tensile stress to a test piece, for use with both existing and novel apparatus for testing the strength, including the tensile strength, of geosynthetic materials.

BACKGROUND OF THE INVENTION

As used herein, the term "geosynthetic material" refers to and connotes, but is not limited to, such materials as woven, braided, or other formed synthetic textile materials, plastics, fiberglass, resinous materials, woven synthetic cloth, matting, webbing, sheeting, composites and mixtures of those materials, and other such materials.

In the design, development and manufacture of geosynthetic materials, it is often necessary to determine the stress resistant characteristics of the material including the material tensile strength.

Prior to the subject invention, a number of devices were available for testing material tensile strength, which devices included various types of grip device for securing a piece in the testing device during the test procedure. Those prior art grip devices provide synchronous activation to engage or release opposing grip members. In the prior art, various means are described to provide replaceable grip members and to provide controlled gripping force to the test piece. Other prior art devices include threaded drive means for engagement and release of opposing grip members. Examples of such structures in the prior art are described in the patents and publications described below.

U.S. Pat. No. 2,600,923 describes a grip device which has manually actuated opposing grip jaws that are engaged or disengaged by operation of a lever mounted on an external surface of the grip device and connected to the separate jaws by various mechanical linkages. The amount of grip force applied to the test piece is controlled and preselected by the operator setting a pin in one of a plurality of registered pairs of force selection holes formed in contiguous members of the grip apparatus parts. The grip jaws of that device are replaceable and mounted on opposing interior faces of grip jaw support members by threaded fasteners, to which access is obtained by partial disassembly of the apparatus. That prior art device permits only incremental variation in the grip force applied to the work piece and does not permit continuous variation in the amount of grip force applied. In addition, removal and replacement of the grip jaws is cumbersome and time consuming.

U.S. Pat. No. 3,247,565 describes grip apparatus in which retaining force is applied to the test piece in a direction transverse to the direction of application of the test force or tensile pull. That apparatus includes one grip member fixed and secured in the body of the device and spaced from an opposing, movable grip member, adjustable by turning two adjusting bolts connected to the movable grip member and rotatably mounted in the frame of the device. That grip apparatus requires manual operation of the adjusting bolts and applies the grip force, not over the full area of the test piece, but rather over limited areas or lines of force on the test piece. In addition, that device does not provide means for overcoming those problems peculiar to gripping tensile stressed geotextile materials including, at least, the necessity to avoid substantial deformation, tearing, slipping, cutting, creep and movement of the test piece.

U.S. Pat. No. 2,350,060 describes a grip device for materials subjected to compression testing, in which the gripping forces are applied along a plurality of tangent lines between grip rollers and the surface of the test piece, with the grip force applied in a direction that is transverse to the direction of the compressive force applied to the test piece. One of two grip blocks remains stationary, with the opposing grip block moved toward the stationary grip block by manual actuation of a pair of adjustment screws connected to the movable block and threadably and rotatably mounted in the frame of the device. That device does not provide means to resolve the problems peculiar to gripping geosynthetic materials during tensile stress testing, including prevention of slip, cutting, tearing, creep and other damage to the test piece.

U.S. Pat. No. 3,461,719 describes a viscoelastometer grip apparatus which addresses problems of creep or slippage of test pieces made of plastic or synthetic resinous materials, especially when tested in high temperature and/or gaseous environments. That grip apparatus includes a pair of opposing grip jaw assemblies, each including oblique walls acting as guide surfaces for contained wedge shaped grip jaws, which apply grip forces in directions oblique to the direction of application of the tensile pull. Easier mounting of the test piece in the opposing grip clamps is enabled by first mounting the opposing grip clamps on a jig which permits one grip clamp to be set in fixed position while the opposing grip clamp is adjusted by movement through a slotted aperture in the jig to permit proper setting of the test and imposition of the initial grip forces to the test piece. Thereafter, the opposing clamps are released from the jig assembly and mounted on the tensile test device for application of the tensile stress to the test piece. Although that device does provide means for mounting and loading test pieces in high temperature, gaseous test environments, that patent does not disclose means for preventing creep and slippage and overcoming test piece damage and deformation in tensile stress testing of geosynthetic materials.

U.S. Pat. No. 2,419,711 describes a tensile test grip device having grip jaw mounting guides within inclined planar surfaces which drive opposing serrated grip jaw pieces toward each other into contact with the peripheral surfaces of a test piece to apply grip forces obliquely to the direction of test force applied to the test piece. That device describes a clamp band surrounding the grip jaw holders and having a threaded set screw extending through the clamp and engaging an outer surface of one of the grip jaw holders to move the grip jaw holders toward each other and to apply the initial, starting grip on the test piece before the test force is applied. That apparatus does not address the particular needs of grip apparatus for tensile testing of geosynthetic materials.

It is an object of this invention to provide grip apparatus for tensile stress testing devices for geosynthetic materials, which grip apparatus is strong and relatively light weight and uses a variety of different size grip jaws which are easily inserted into, removed from or replaced in the grip jaw support members of the apparatus without requiring substantial disassembly of the apparatus.

It is a further object of this invention to provide such grip apparatus for geosynthetic materials to substantially reduce damage to the test piece by providing opposing grip jaw structures which can be actuated and moved selectively either in mutually synchronous relationship or in asynchronous relationship to provide engagement with a test piece.

Another object of this invention is to provide grip apparatus for geosynthetic materials in which at least one of the grip jaws can be selectively preset in a stationary position and the opposing grip jaw can be carefully actuated by controlled application of relatively small force increments systematically applied to the movable grip member to assure effective gripping of the test piece while avoiding creep, slippage, deformation or damage to the test piece.

Another object of this invention is to provide grip apparatus for stress testing of geosynthetic materials wherein the grip members are actuated by fluids in a controlled manner to apply either continuous or relatively small increments of actuating force selectively at separate points on the test piece.

SUMMARY OF THE INVENTION

In accordance with the present invention, there is provided a geosynthetic material test piece grip apparatus that includes a frame comprising two opposing end members and two opposing side members, all connected to form a rectangular frame; first and second opposing grip assemblies slidable within the frame; first and second adjusting assemblies for each of the first and second grip assemblies, respectively. In a preferred embodiment of this invention, the apparatus includes, an adjustable lock assembly mounted on the frame to hold the first grip assembly stationary during engagement or disengagement with the second grip assembly to secure or release the test piece.

In a preferred embodiment of the apparatus of this invention, either one, or both, of the separate adjusting means for the first grip assembly and for the second grip assembly are actuated by fluid driven actuating means.

In a further preferred embodiment of this invention, the fluid actuated first adjusting means and second adjusting means for the first and second grip assemblies are separately and automatically actuated in response to analysis of grip force data and test piece data received, transmitted and analyzed by a servo-mechanism.

In another preferred embodiment of this invention, each grip assembly includes a grip bar slidably mounted in opposing channels formed in the interior surfaces of the frame side members, with each grip bar having at least one channel formed in its surface facing the other grip assembly, with a readily replaceable grip jaw slidably mounted in the grip bar channel.

In a further preferred embodiment of this invention, each of the grip assembly grip bars has formed in one of its surfaces a plurality of nested grip bar channels of varying widths, all of the channels having a common central transverse axis through the channels.

In another preferred embodiment of this invention, the central transverse axis of each of the grip bar channels formed in the grip bar carrier is perpendicular, or substantially perpendicular, to the longitudinal axis of the grip bar.

, In another preferred embodiment of this invention, each grip bar has formed in its working surface at least one groove, in which is mounted a grip rod coated with a bonded particulate, or other high friction grip material.

BRIEF DESCRIPTION OF THE DRAWINGS

FIG. 4 is an isometric view of two opposing grip bars suitable for use with this invention, in which each grip bar has a plurality of nested channels, all having a common central transverse axes, and each channel adapted to secure or contain a grip jaw.

FIG. 5 is an isometric view of the working surface of a grip jaw adapted for mounting on the grip bar shown in FIG. 4.

FIGS. 6a through 6d, inclusive, are isometric views of the reverse side of a plurality of grip jaws such as the grip jaw shown in FIG. 5 and depicting the varying dimensions of such grip jaws, each adapted for mounting in a particular channel formed in the grip bar depicted in FIG. 4.

FIG. 7 is a view taken in vertical cross-section of a grip jaw as shown in FIGS. 5 and 6 connected by a threaded fastener to the grip bar shown in FIG. 4.

DESCRIPTION OF THE PREFERRED EMBODIMENTS

Figure 1:
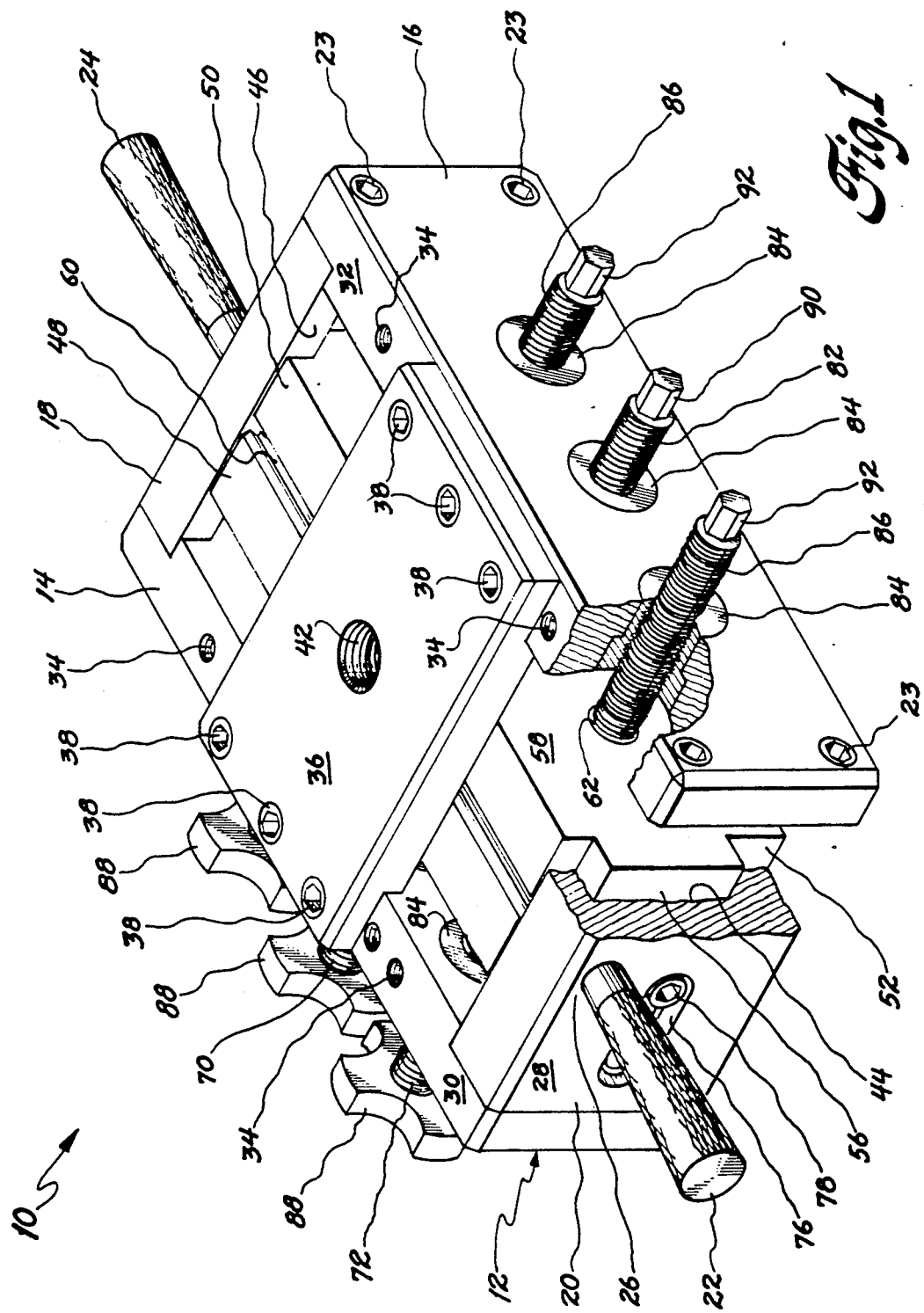
FIG. 1 is an isometric view of an embodiment of the apparatus of this invention.

One embodiment of the apparatus of this invention is shown in FIG. 1, wherein the grip assembly, indicated generally by reference numeral 10, consists of a frame indicated generally by reference numeral 12, including opposing first and second side members 14 and 16 and opposing first and second end members 18 and 20. The side and end members of frame 12 are connected at their corners by threaded fasteners 23 secured in threaded bores 21.

Each of the end members 18 and 20 has connected to a top portion 26 on its front surface 28 a transport means, shown in FIG. 1 as handles 22 and 24.

Each of side members 14 and 16 has a top surface 30 and 32, respectively, in each of which there is formed a plurality of threaded bores 34 in spaced alignment along each of top surfaces 30 and 32. Means for connecting grip assembly 10 to appropriate tensile strength testing apparatus includes connecting plate 36, mounted on the top surfaces 30 and 32 of side members 14 and 16 by threaded fasteners 38, secured in threaded bores 40, each of which is aligned with one of the threaded bores 34 formed in the top surface 30 or 32 of side members 14 and 16. A suitable number of threaded bores 34 and 40, and threaded fasteners 38, are provided on frame members 14 and 16 to accommodate connecting plates 36 of different sizes, as determined by the size of grip apparatus 10 and the size of the tensile stress testing device which must be employed.

A central threaded bore 42 extends through connecting plate 36 in co-axial alignment with the central axis through connecting plate 36. Connecting bore 42 is constructed and arranged to engage a threaded fastener or other appropriate fastening member adapted to permit rapid and easy mounting and demounting of grip apparatus 10 from the tensile strength testing apparatus.

As shown in FIG. 1, each end member 18 and 20 has a longitudinal channel 44 formed in its interior surface 46. A first grip bar 48 and a second grip bar 50 are each slidably mounted in and between the end members 18 and 20. Each grip bar 48 and 50 has formed on each of its longitudinal end portions 52 a shoulder 56 extending outwardly from end surface 52 of grip bar 48 and 50 into slidable engagement with channel 44 in end members 18 and 20.

As is described more fully below, each grip bar 48 and 50 has mounted thereon a grip jaw 60 which is shown partially in FIG. 1 on the surface of first grip bar 48 facing second grip bar 50.

Figure 2:
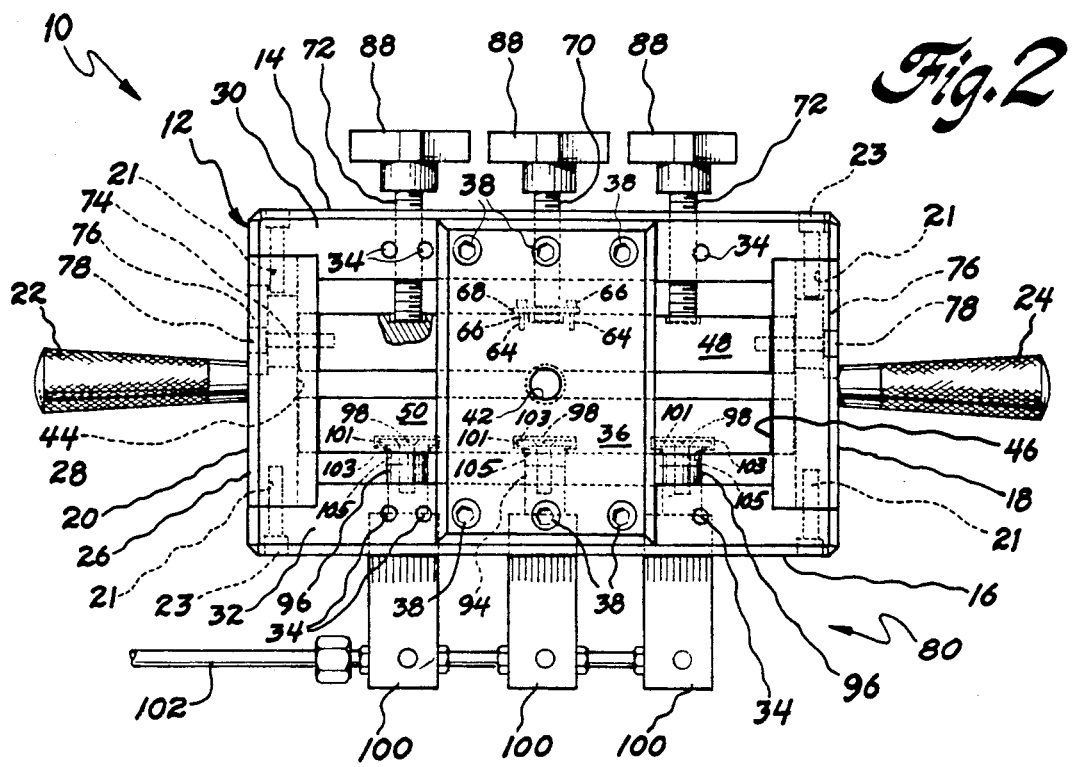
FIG. 2 is a top plan view of another embodiment of this invention, having fluid activated actuators attached to one grip bar.

Shown in FIGS. 1, 2 and 4, each grip bar 48 and 50 has formed in its rear surface 58, a plurality of mutually aligned and spaced counter-sunk seating surface 62 and 63.

As shown in FIG. 4, at least one of the counter sunk seats 63 is oriented substantially co-axially with the central portion of the rear surface 58 of grip bar 50. A pair of threaded bores 64 are located on either side of central seat 63. Each threaded bore 64 receives a threaded fastener 66 extending through a flange 68 formed on the end of a central second adjusting shaft 82 attached to second grip bar 50.

As shown in FIGS. 1 and 2, a plurality of first adjusting shafts 70 and 72 are connected to, or are in contact with, the rear surface of first grip bar 48. In addition to a central first adjusting shaft 70, there are rotatably mounted in side member 14 two additional first adjusting shafts 72 and 72, which are substantially equally spaced in either side of central first adjusting shaft 70 and which are threaded for rotational advancement in and out of side member 14 of frame 12. Although first adjusting shafts 72 can be advanced into the interior of frame 12 to provide contact between the inner end of each first adjusting shaft 72 and its corresponding counter sunk seat 63 in first grip bar 48, first adjusting shafts 72 do not have their inner ends connected to first grip bar 48. However, the inner end of central first adjustment shaft 70 is connected in seat 63 to first grip bar 48 by threaded fasteners 65 in bores 61. That construction enables easy disengagement of the first adjusting shafts 72 from contact with first grip bar 48 while the central first adjusting shaft 70 is employed to move first grip bar 48 toward, or away from, the working surface of second grip bar 50 and a test specimen that is engaged between the opposing work surfaces of first and second grip bars 48 and 50.

Another advantage in use of the apparatus of this invention is inherent in having only the central first adjusting shaft 70 connected to first grip bar 48 while the other first adjusting shafts 72 are maintained merely in contact with the rear surface of first grip bar 48. The gripping force applied to first grip bar 48 can be applied initially through first actuator shaft 70 and then applied additionally through each or both of the other first actuator shafts 72, either to the same degree of force, or in differing degrees of gripping force applied through each of the actuator shafts 70 and 72. The ability to apply gripping forces to the test specimen in that manner is particularly beneficial when geosynthetic materials are being gripped for testing to permit the application of effective grip force to such geosynthetic material specimen while avoiding creep, deformation, slipping, cutting or other adverse effects that are deleterious to the test results.

A similar structure, described more fully below, exists with respect to the second adjusting shafts and second grip bar 50, with similar advantages providing an enhanced, substantial degree of control in application of gripping forces and in enabling gradual and varying application of uniform or individual gripping forces to various points along a geosynthetic test specimen to avoid creep, slipping, cutting, tearing or deformation of the test specimen with deleterious effects upon the test results.

As shown in FIGS. 1 and 2, one preferred embodiment of the apparatus of this invention includes structural members that enable adjustment and subsequent stationary fixation of first grip bar 48 in a preselected, desired position adapted to provide effective gripping of a test specimen and rapid and easy release of gripping forces to permit easy removal and replacement of test specimens without a multiplicity of adjustments of a plurality of structural members in the grip apparatus. As shown in FIGS. 1 and 2, there is formed in each shoulder 56 of first grip bar 48 a locking bore 74, aligned with an elongated locking slot 76 formed in the outer surface 28 of each of the end members 18 and 20. A locking pin 78 extends from locking slot 76 through side member 18 or 20 into locking bore 74 in shoulder 56 of first grip bar 48.

In use, while the position of first grip bar 48 is being selected and set, and, in other appropriate circumstances, while all or a portion of the desired grip forces are being applied to first grip bar 48, the locking pins 78 are not inserted, or at least are not tightened, in locking slots 76 and locking bore 74.

After the desired position of first grip bar 48 is established, and, in other appropriate circumstances, after the desired amount of gripping force is applied through adjusting shafts 70 and 72 to first grip bar 48, locking pins 78 are inserted and tightened in locking slots 76 and locking bores 74 to prevent relative motion between each end portion 52 of first grip bar 48 and its adjacent end member 18 or 20. Alternatively, when desired in particular circumstances, the use of the locking means 74, 76 and 78 for first grip bar 48 can be ignored and the opposing grip bars 48 and 50 can be moved simultaneously, or intermittently, either synchronously or asynchronously, toward and away from each other during use of the grip apparatus.

In another alternative structure of the apparatus of this invention, central first adjusting shaft 70 is not fixedly connected to first grip bar 48, but merely makes contact with first grip bar 48, in the same manner as is done with the other first adjusting shafts 72. In that embodiment, movement of first grip bar 48 toward second grip bar 50, and application grip force to first grip bar 48, is imparted by actuation of first adjusting shafts 70 and 72. Rearward adjustment of first grip bar 48, and its movement away from second grip bar 50, is done manually or by manual adjustment of the test specimen held between first and second grip bars 48 and 50.

Figure 3:
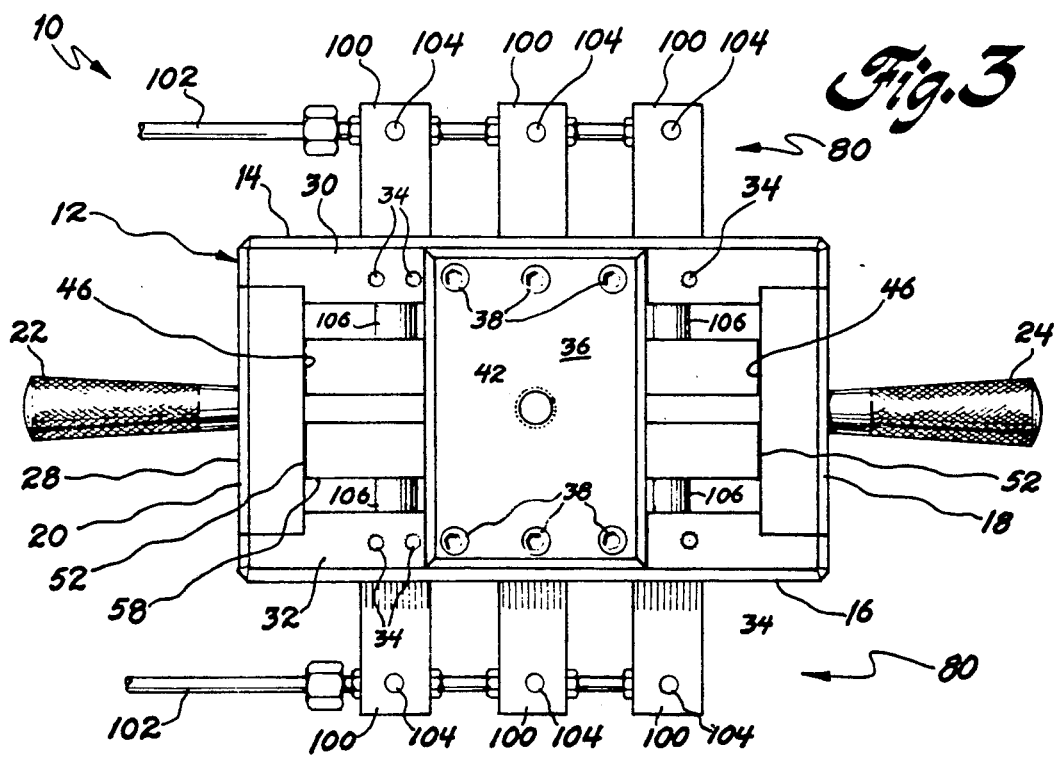
FIG. 3 is a top plan view of another embodiment of the apparatus of this invention having both grip bars operated by fluid activated actuators.

The second actuating means used to move and impart gripping forces to the second grip bar 50 is shown in various embodiments in FIGS. 1, 2 and 3 and is referred to generally by reference numeral 80 in FIG. 2 and 3. Referring to FIG. 1, a central second adjusting shaft 82 extends through side wall 16 of frame 12 and is mounted in a threaded bushing 84 constructed of brass or other suitable material. Similar to the structural elements connecting central first adjusting shaft 70 to first grip bar 48, the inner end of the central second adjusting shaft 82 seats in a central counter-sunk seat 63 in the rear surface 58 of second grip means 50, and is connected thereto by a pair of threaded fasteners 66 extending through holes 67 in a flange on the end of central second adjusting shaft 82 and extending into threaded bores 64 in the rear surface 58 of second grip bar 50. In certain particular embodiments of the apparatus of the apparatus of this invention, the central second adjusting shaft 82 is not connected to the rear surface 58 of second grip bar 50, but merely in adjustable to make contact with that surface, without being connected thereto.

In FIGS. 1 and 2, second adjusting shafts 86 are rotatably mounted in brass bushings 84 extending through side member 16 and having their inner end portions seated in counter sunk seats 62 in second grip bar 50.

In use, the operation of second adjusting shafts 82 and 86 to move, and apply gripping force to, second grip bar 50 is similar to the operation of first adjusting shafts 70 and 72 in the movement of, and application of grip forces to, first grip bar 48. Central second adjusting shaft 82, connected to second grip bar 50 moves second grip bar 50 toward and away from the opposing first grip bar 48 for engagement, or release, of a test specimen and application of grip force. An initial gripping force can be applied through central second adjustment adjusting shaft 82, with additional gripping forces, all of the same magnitude or of differing and separate magnitudes, applied through second adjusting shafts 86.

As shown in FIGS. 1 and 2, each of the first adjusting shafts 70, and 72 have mounted on their external ends a handle 88 for manual actuation of the adjusting shaft. In FIG. 1, the exterior ends 90 and 92 of each of the second adjusting shafts 82 and 86 terminate in an integral extension of the shaft, having a polygonal transverse cross-section adapted for actuation by a torque wrench or similar device and also adapted alternatively for connection to a fluid driven adjusting shaft actuating means indicated generally as 80, in FIGS. 1 and 3.

In the embodiment shown in FIG. 1, a fluid driven actuator can be connected by suitable mechanical linkage to the polygonal end portions 90 or 92 of each of the second adjusting shafts 82 and 86. In the embodiment of the invention shown in FIG. 2, the second adjusting shafts 94 and 96 are slidably secured within side member 16. As shown in FIG. 2, the end of the each adjusting shaft 94 and 96 is threadably connected to a threaded connecting pin 98, the head 101 of which seats in a slot 103 formed in the bottom surface of second grip for 50. Alternatively, only the central slidable second adjusting shaft 94 is fastened at its end to second grip bar 50, with the two adjoining slidable second adjusting shafts 96 being operable to make contact with the rear surface of second grip bar 50 without being connected thereto.

In FIG. 2, each of the second actuating shafts 94 and 96 is part of, or an extension of, a fluid driven piston actuated by a fluid pump 100 shown in FIGS. 2 and 3. The actuating fluid used with pump 100 can be air or another gas. In a preferred embodiment of this invention, pump 100 is actuated by an hydraulic liquid. Use of hydraulically actuated pumps 100 enables better controlled and smoother application of gripping forces to the test specimen and also enables application of both greater gripping forces and smaller, better controlled incremental changes in gripping force, than those attainable with pneumatically actuated pumps 100.

Hydraulic pumps 100 found particularly suitable for use with this invention include HYTEC air/hydraulic pumps manufactured by Ottawa Tool Company of Ottawa, Canada. In those pumps, pneumatic pressure delivered to the pump is internally transducted into hydraulic pressure delivered by the pump to the piston-/adjusting shaft 94, 96. HYTEC air/hydraulic pump model No. 100190 has an hydraulic to pneumatic pressure conversion ratio of 39:1, delivering approximately 4,875 psi hydraulic for applied air pressure of 125 psi. HYTEC pump model No. 100174, having an hydraulic to air pressure conversion ratio of 25:1 delivers approximately 3,125 psi for an impressed air pressure of 125 psi. Those pumps have proved preferable for application of substantially higher gripping forces, as well as demonstrating smooth increase and decrease of the grip forces without damaging the test specimen or inducing deformation, slippage or creep of the test specimen.

As shown in FIG. 2, the actuating fluid for pumps 100 is delivered through fluid conduits 102, which are connected to a reservoir (not shown in the drawing) of actuating fluid. As shown in FIGS. 2 and 3, fluid conduits 102 can provide a uniform stream of drive fluid to each of the pumps 100 for continuous and simultaneous application of equal grip forces through all of the pumps. Shown diagrammatically on each of the pumps 100 in FIGS. 2 and 3 is a valve means 104, each of which is individually actuated and adjusted to provide for individual, synchronous or asynchronous, and intermittent or continuous, actuation of one or all of the pumps 100, with the selective application of equal or differing grip forces through each or all of the pumps 100, as required in testing a particular test specimen. Alternatively, separate, asynchronous selective operation of each or all of the pumps 100 is enabled by connecting each pump 100 to a separate source of actuating fluid.

FIG. 3 depicts another embodiment of the apparatus of this invention in which both first grip bar 48 and second bar 50 are fluid actuated by pumps 100. In that embodiment, the first adjusting shafts 70 and 72 shown in FIG. 2 for operation in conjunction with first grip bar 48 are replaced by slidable first adjusting shaft pistons 106 shown in FIG. 3. The alternative means of connecting first adjusting shafts 106 and their means of operation, are similar to the means of connecting (101 and 103) and operating second adjusting shafts 94 and 96 shown in FIG. 2. The apparatus shown in FIG. 3, in which first grip bar 48 is fluid actuated, is particularly useful in circumstances in which the locking means associated with first grip bar 48 are not used in setting, gripping, testing, releasing and replacing a test specimen.

The apparatus of this invention providing a plurality of at least three adjusting shafts for use with each of the first and second grip bars provides substantial advantages, not provided by previously existing devices, for effective testing of a wide range of geosynthetic materials, produced in many variations of form and texture, without creep, slipping, or damage to the test specimen. For example, the apparatus of this invention has been used effectively for tensile strength testing of geosynthetic materials including thick matted materials woven of synthetic fibers; thin, closely woven geosynthetic cloth-like materials having a single strand thickness; webbed plastic materials and webbed metallic materials. The ability to apply the same or differing forces through a plurality of adjusting shafts is also useful for effective test gripping of geosynthetic and other materials having irregular surfaces, thicknesses or configurations.

In another preferred embodiment of the apparatus of this invention, actuation of the first and second adjusting shafts and actuating pumps 100 is controlled by a computerized digital/analog servomechanism, having sensors connected at selected points on the test specimen to monitor the specimen for deformation, creep or slippage. The monitoring sensor signals provide input data for the computerized servomechanism, which generates output control signals fed to each of the pumps 100 driving the first and second adjusting shafts.

Various types of grip jaws 60, suitable for use with this invention, are shown in FIGS. 4 through 11, inclusive. FIG. 4 shows grip bars 48 and 50 having formed in their opposing working faces a plurality of nested channels; for example, 108 and 110, each adapted to receive an appropriately sized grip jaw, such as 112 and 114, as shown in FIGS. 5, 6 and 7. Grip jaw channels 108 and 110, and grip jaws 112 and 114, are each constructed in accordance with standard, industry accepted sizes such as one inch width, two inch width, etc.

As shown in FIG. 4, the nested grip jaw channels such as 108 and 110 share a common central transverse axis which is substantially coincidental with the central transverse axis of their respective grip bar 48 and 50. That construction enables balanced, symmetric application of grip forces. In another preferred embodiment of this invention, grip bars 48 and 50 can be provided with a plurality of aligned, nested grip bar channels, or with a plurality of non-aligned, asymmetrical grip bar channels, depending upon the geosynthetic or other material tested and the type of test to be performed.

Each of the grip bars 48 and 50 has extending therethrough a plurality of bores 116, located near the bottom of the grip bar channels 108 and 110. For alignment with respective, adjacent bores 116, each of the grip jaws 112 and 114 has one or more holes 118 therethrough, to receive an allen head fastener 122, shown in FIG. 7 secured in opening 116 through second grip bar 50, with the threaded end of fastener 122 secured in the opening 118 of grip jaw 114.

Any means of securing the grip jaw 112 of 114 in the grip bar channel 108, or 110, which is sufficient to sustain the forces and stresses encountered during testing, is suitable for use with the apparatus of this invention.

Figure 8:
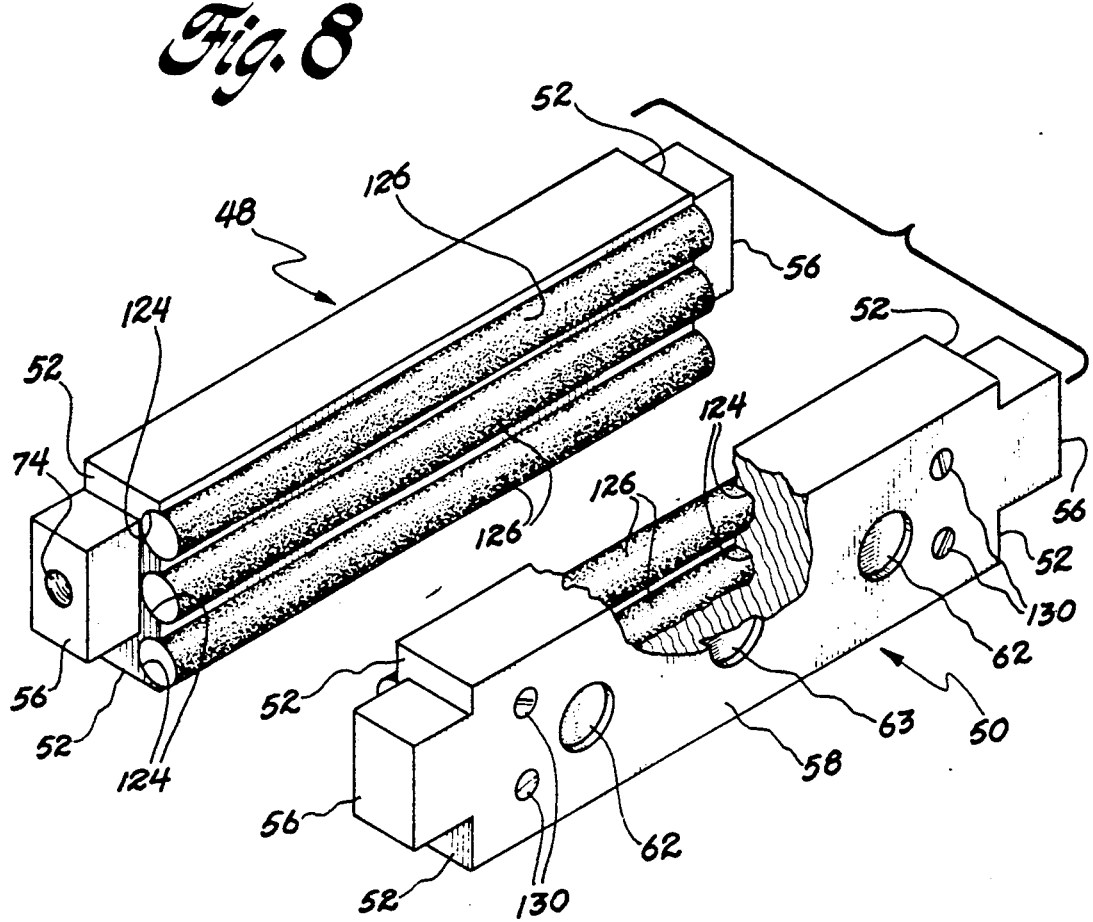
FIG. 8 is an isometric view of an opposing pair of grip bars, with one view show in partial, cut away cross section, depicting a grip jaw having a plurality of longitudinal grooves formed in the working face of the grip bar and having an elongated grip rod mounted in each groove, with the grip rod coated with a particulate gripping material adapted to provide a substantial friction grip of a test specimen.
Figure 9:
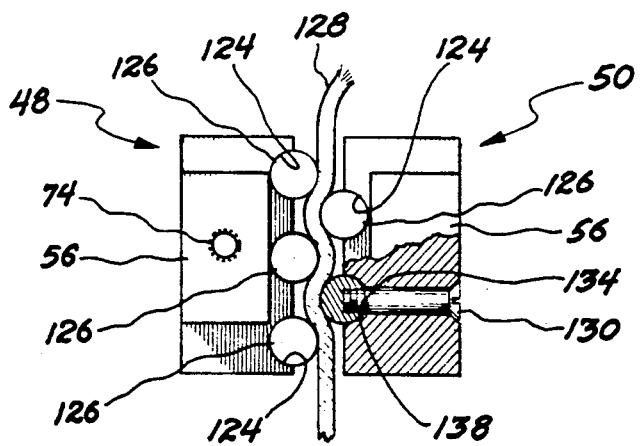
FIG. 9 is an end elevation view, partially in cross-section, of the opposing grip bars of FIG. 8 and showing one preferred method of connecting the grip rod to the grip groove by a threaded fastener.

Another grip bar structure 60 suitable for use with this invention is shown in FIGS. 8 and 9. Grip bars 48 and 50 each have a plurality of grooves 124 formed in their opposing working surfaces. As shown in that particular embodiment, the longitudinal axes of the grooves are substantially parallel; however, other configurations and arrangements of the grip jaw grooves 124 can be used with this invention. For example, although grooves 124 are shown in FIGS. 8 and 9 as being semicircular in transverse cross-section with a smooth arcuate surface concave outwardly from the working surface of the grip bar, the groove transverse cross-section can be polygonal in circumstances in which that construction is desirable, for example, when more effective contact is desired between the surface of the groove and a contiguous surface of another structural element.

In one embodiment of this invention, particularly when bulky or substantially compressible materials are being tested, the grip bars 48 and 50 shown in FIGS. 8 and 9 have no other grip structural elements mounted in the grooves 124. In that embodiment, gripping action between the working surfaces of grip bars 48 and 50 and the test specimen is effected by the flat working surface of one grip bar forcing the bulky, compressible test specimen into the groove of the working surface of the opposing grip bar, with those gripping, compressive forces alternating back and forth between the pairs of grip bars along their adjacent working surfaces.

In the grip bars as shown in FIGS. 8 and 9, each of the grooves 124 has secured therein a grip rod 126. Grip rod 126 is composed of a material, or is coated with a material, having a substantial index of friction. One such suitable material is a particulate, multifaceted material having a plurality of sharp angles on each particle, which applies a "gritty" surface to the test specimen 128, in FIG. 9. Although the grip rod 126 is shown in FIGS. 8 and 9 as having a circular transverse cross-section, that cross-section also can be polygonal in circumstances where such configuration provides more secure mounting of grip rod 126 in groove 124, or when a grip of polygonal cross-section provides better gripping action for test specimen 128.

Grip rods 126 can be glued or bonded into grooves 124 on the grip bars 48 and 50. A structure permitting easier replacement of grip bars 126 is shown in FIGS. 8 and 9 wherein a grip rod connecting pin 130, having a threaded end portion, is secured in a bore 132 in grip bar 50, with the threaded portion 134 of pin 130 secured in a threaded bore 138 formed in grip rod 126.

Figure 10:
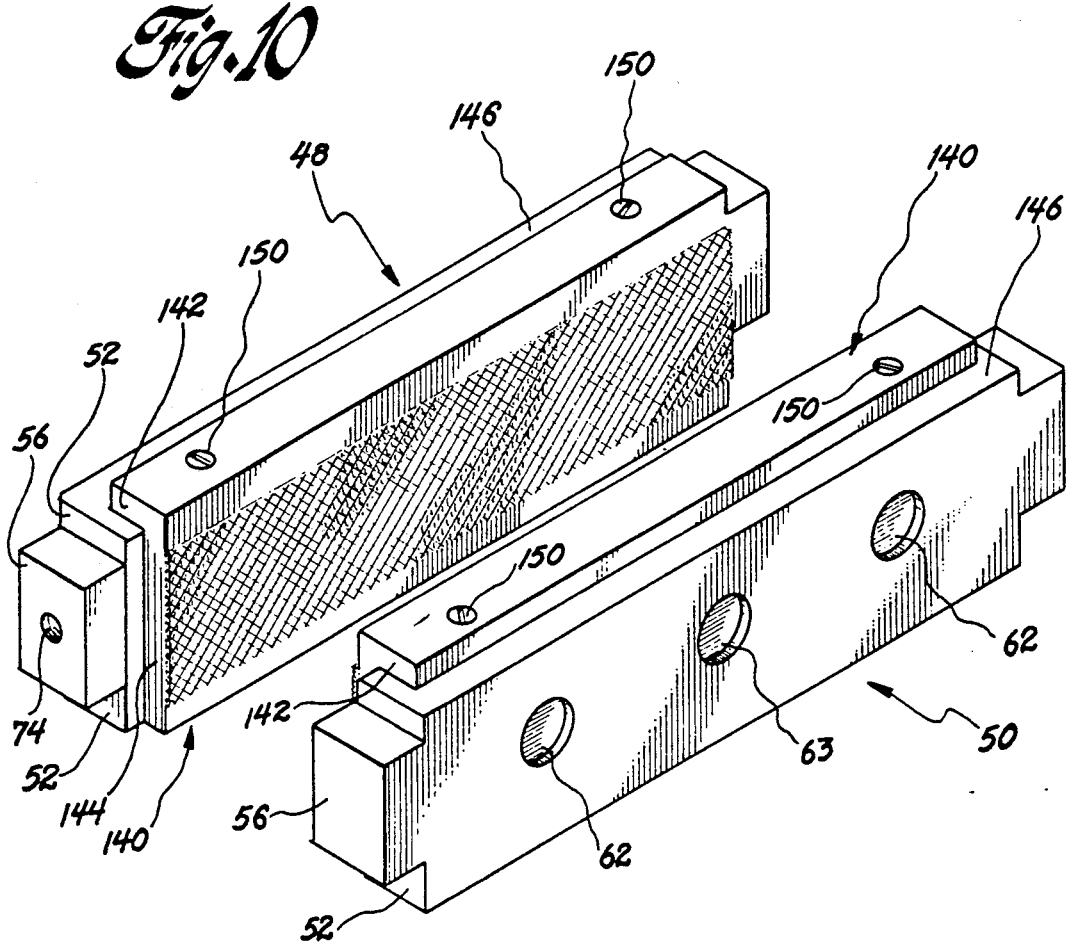
FIG. 10 is an isometric view of an opposing pair of grip bars, each having mounted thereon an L-shaped grip jaw having a rearwardly depending shoulder connected to the top surface of the grip bar.
Figure 11:
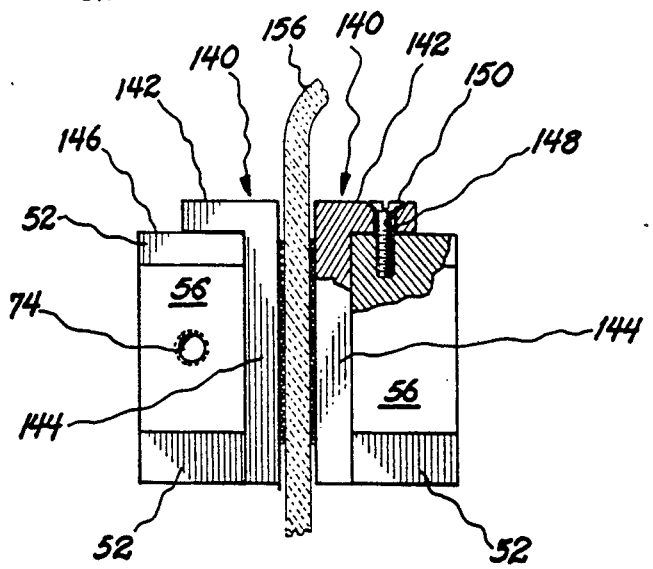
FIG. 11 is an end elevation, in a partial cross-section, showing the opposing grip bars and grip jaws of FIG. 10 engaging a test specimen and depicting the connection of a grip bar to the grip jaw use of a threaded fastener.

Another grip jaw structure 60 suitable for use with this invention is shown in FIGS. 10 and 11. An L-shaped grip jaw 140 has a top shoulder 142 integral with a body 144 depending or extending away from the shoulder 142 substantially at a right angle with the shoulder 142. Shoulder 142 rests upon the top surface 146 of each of the grip bars 48 and 50. Each of the shoulders 142 of grip bar 140 has extending therethrough a pair of bores 148 to receive a threaded fastener 150, having its end 152 threadably secured in a similar bore 154 in the top of the grip bar 48 and 50, aligned with one of the bores 148 in shoulder 146. In certain embodiments of this invention, in which the grip forces or other test conditions allow it, the grip jaws 140 can be used without using the fasteners 150 to secure the shoulders 142 to the top surfaces 146 of the grip bars 48 and 50.

As shown in FIG. 10, the working surface of grip jaw 140 consists of a cross-hatched, hard metallic surface providing a plurality of sharp, pointed pyramidal "teeth", similar to the surface of a file, for engaging the surface of a work piece 156. In other particular embodiments of this invention, grip jaw 140 can incorporate other gripping structures such as the plurality of parallel grooves and ridges shown in FIG. 5; the plurality of "gritty" grip rods as shown in FIG. 8 or the plurality of alternating grooves and flat surfaces shown and discussed with respect to FIGS. 8 and 9. One advantage often realized in using the grip structure of grip jaw 140, with or without the grip jaw fastened to the top surface of the grip bar, arises when the grip jaw 140 and connecting plate 36 are so constructed that there is sufficient vertical distance between connecting plate 36 and the other structural members that grip jaw 140 can be removed from grip bar 48 or 50, and replaced, without removing connecting plate 36 from frame 12, and without removing grip assembly 10 from the tensile strength testing apparatus. In one embodiment of this invention having easily replaceable grip jaws, either or both of grip jaw shoulder 142 and grip bar upper surface 146 have magnetic portions that retain the grip jaw in place until force is applied manually or with a small tool to remove the jaw.

According to the provisions of the patent statutes, I have explained the principle, preferred construction and mode of operation of my invention and have illustrated and described what I now consider to represent its best embodiments. However, it should be understood that, within the scope of the appended claims, the invention may be practiced otherwise than as specifically illustrated and described.

Therefore I claim:

1. Grip apparatus for use with tensile strength testing apparatus adapted to measure the tensile strength of a specimen comprising
    a frame having a pair of opposing first and second side members and a pair of opposing first and second end members, and
    a first grip assembly movably mounted in the frame between said end members for movement between the side members, and
    first adjustment means mounted on first side member of the frame with a portion of said first adjustment means extending outwardly beyond the external surface of said first side member, and
    said first adjustment means having an inner portion extending within said frame in contact with a surface of said first grip assembly, and
    with said first adjustment means constructed and arranged to move said first grip assembly along a path between said end members selectively toward or away from said first side member of the frame, and
    a first actuator means connected to said first adjustment means, and
    a second grip assembly movably mounted between the end members of the frame toward and away from said first grip assembly, and
    second adjustment means mounted in said second side member of the frame and having a portion extending outwardly beyond the exterior surface of said second side member, and
    with said second adjustment means having an inner portion extending inwardly within said frame beyond the interior surface of said second side member and engaging said second grip assembly to move said second grip assembly along a path between said end members, and
    a second actuator means to actuate said second adjustment means connected to said second adjustment means, and
    lock means connected to said first grip assembly and movably mounted within said first and second members of the frame to enable selective adjustment and selected stationary fixation of the position of said first grip assembly with relation to its distance from the side members of the frame, and
    connecting means mounted on said frame for connecting said grip apparatus to said tensile strength testing apparatus.

2. Apparatus as described in claim 1 wherein said connecting means comprises a connecting plate mounted on top of said frame and having means on said connecting plate adapted to engage a connecting member mounted on said tensile strength testing apparatus.

3. Apparatus as described in claim 1, wherein said lock means comprises
    a pair of elongated opposing lock openings in mutual alignment each formed in, and extending through, a separate one of the two side members of the frame, and
    a pair of lock bores, each formed in one separate end of said first grip assembly in alignment with a portion of a separate one of said lock openings formed in a side member of the frame, and
    a lock pin secured in said lock opening in said side member and extending into said lock bore in the adjacent end of said first grip assembly, with said lock pin adjustable to prevent relative motion between the first grip assembly and the contiguous frame end member.

4. Apparatus as described in claim 1 wherein said first adjustment means comprises
    a plurality of mutually spaced and aligned bores extending through said first side member adjacent said first grip jaw assembly, and
    a plurality of first adjustment shafts, each secured in a separate one of said bores in said first side member, and having the inner end of one of said first adjusting shafts connected to said first grip assembly and the inner ends of the other first adjusting shafts constructed and arranged for unconnected contact with the surface of said first grip assembly, and said plurality of first adjusting shafts having their respective ends distal from said first grip assembly extending outwardly from the exterior surface of said frame first side member, and
    first actuator means connected to said distal end of each of said first adjusting shafts to apply force to each of said first adjusting shafts and said first grip jaw assembly.

5. Apparatus as described in claim 4, wherein one of said first adjusting shafts connected to said first grip assembly is connected at substantially the center point of the connection surface of said first grip jaw assembly.

6. Apparatus as described in claim 4, wherein said first actuator means includes a plurality of fluid actuated means each attached to a separate one of each of said first adjusting shafts to selectively move each of said first adjusting shafts.

7. Apparatus as described in claim 1 and including first actuator means connected to said first adjustment means to impart force through said first adjustment means to said first grip bar, and second actuator means connected to said second adjustment means to impart force through said second adjustment means to said second grip bar.

8. Apparatus as described in claim 7, wherein each of said first and second actuator means includes a plurality of fluid driven actuator means, each attached separately to one of each of said first and second adjusting shafts.

9. Apparatus as described in claim 7, wherein each of said first and second actuator means is actuated by hydraulic fluid.

10. Apparatus as described in claim 7, wherein each of said first and second actuator means is pneumatically actuated and internally traduces the pneumatic force to hydraulic force imparted to said first and second adjusting shafts.

11. Apparatus as described in claim 7, wherein each of said first and second actuator means is selectively and independently actuated to impart separately determined amounts of movement and force to each of said first and second adjusting shafts.

12. Apparatus as described in claim 1 wherein said second adjustment means comprises
    a plurality of openings formed in and extending through said second side member, and
    a plurality of second adjusting shafts, each mounted in a separate one of said openings through said second side member, and
    one of said second adjusting shafts connected at its interior end to substantially the center of the adjacent surface of the second grip assembly, and
    the remaining second adjusting shafts having their interior ends constructed and arranged for unconnected, selective contact with the adjacent surface of the said second grip assembly.

13. Apparatus as described in claim 1, wherein said lock means is selectively releasable and engageable to place said grip assembly in a stationary position within said frame while said second grip assembly is moved between said side members by said second adjustment means into engagement and disengagement with a test specimen held between said first and second grip assemblies.

14. Apparatus as described in claim 1, wherein each of said first and second grip assemblies comprises,
    a grip bar slidably mounted in channels formed in the interior surfaces of the opposing frame end members, and
    a grip jaw mounted on the surface of said grip bar facing an opposing grip bar.

15. Apparatus as described in claim 14, wherein each grip bar has formed therein a plurality of nested channels, all having a common central transverse axis substantially perpendicular to the longitudinal axis of said grip bar, and
    each of said grip bars has a grip jaw mounted within one of said nested channels.

16. Apparatus as described in claim 14, wherein said grip jaw has a plurality of alternating ridges and grooves formed in the grip jaw surface facing the opposing grip jaw.

17. Apparatus as described in claim 14, wherein each of said grip bars has formed on the surface thereof facing the opposing grip bar at least one elongated groove facing the opposing grip bar.

18. Apparatus as described in claim 17 and including at least one elongated rod mounted said elongated groove, said rod having an exterior surface coated with particles adapted to provide a substantial friction grip on the surface of a test specimen held between the opposing grip jaws.

19. Apparatus as described in claim 14 wherein each of said grip jaws comprises
    a body member having a grip element formed on the surface thereof facing the opposing grip jaw, and
    a top portion extending from the top end of the body membered rearwardly along the top surface of the contiguous grip bar.

20. Apparatus as described in claim 1 and including transport means mounted on said frame to facilitate carrying, installation and removal of said textile grip apparatus.

21. Apparatus as described in claim 20, wherein said transport means includes a pair of handles.

22. In apparatus for testing the tensile strength of a test specimen, test specimen grip apparatus comprising
    a frame having a pair of opposing side portions and a pair of opposing end portions, and
    first grip means slidably mounted between the frame end portions for movement toward and away from said frame side portions, and
    first adjustment means mounted on the frame and arranged for selective contact with said first grip means, and
    first actuator means connected to said first adjustment means for imparting movement of, and grip force through, said first adjustment means to said first grip means, and
    second grip means movably mounted between said frame end portions and opposite said grip means, and second adjustment means mounted in the frame and arranged for selective contact with said second grip means, and
    second actuator means connected to said second adjustment means to impart movement of, and grip force through, said second adjustment means to said second grip means, and
    releasable locking means mounted on said first grip means and slidably connected to said frame to enable selective adjustment and stationary fixation of the position of said first grip means with respect to its distance from said second grip means, and
    grip apparatus connecting means mounted on said frame to engaged connecting means mounted on said testing device.

23. For use with a test tensile strength testing apparatus, grip apparatus comprising
    a grip bar having a working surface, and
    a plurality of nested channels formed in the working surface of said grip bar,
    all of said nested channels having a common central transverse axis substantially perpendicular to the longitudinal axis of said grip bar, and a grip jaw mounted within one of said nested channels.

24. Apparatus as described in claim 23 wherein the common central transverse axis of said nested channels is substantially coincidental with the central transverse axis of said grip bar.

25. Apparatus as described in claim 23 wherein said grip jaw has a working grip surface comprising a plurality of alternating ridges and grooves formed in its grip surface.

26. Apparatus as described in claim 23 wherein said grip jaw comprises at one groove formed in, and concave outwardly from, said working surface of said grip bar.

27. Apparatus as described in claim 26 wherein said groove has mounted therein a grip member having a gritty surface.

28. Apparatus as described in claim 23, wherein said grip jaw has a grip surface comprised of plurality of pyramidal, outwardly pointing teeth formed by a plurality of cross-hatched ridges formed in said working grip surface.

29. Grip apparatus for use with tensile strength testing apparatus adapted to measure the tensile strength of a specimen comprising
- a frame having a pair of opposing first and second side members and a pair of opposing first and second end members, and
- a first grip assembly movably mounted in the frame between said end members for movement between the side members, and
- first adjustment means mounted on first side member of the frame with a portion of said first adjustment means extending outwardly beyond the external surface of said first side member, and
- said first adjustment means having an inner portion extending within said frame in contact with a surface of said first grip assembly, and
- with said first adjustment means constructed and arranged to move said first grip assembly along a path between said end members selectively toward or away from said first side member of the frame, and
- a first actuator means connected to said first adjustment means, and
- a second grip assembly movably mounted between the end members of the frame toward and away from said first grip assembly, and
- second adjustment means mounted in second side member of the frame and having a portion extending outwardly beyond the exterior surface of said second side member, and
- with said second adjustment means having an inner portion extending inwardly within said frame beyond the interior surface of said second side member and engaging said second grip assembly to move said second grip assembly along a path between said end members, and
- a second actuator means to actuate said second adjustment means connected to said second adjustment means, and
- connecting means mounted on said frame for connecting said grip apparatus to said tensile strength testing apparatus.

* * * * *